United States Patent
Joung

(10) Patent No.: US 9,953,463 B2
(45) Date of Patent: Apr. 24, 2018

(54) RADIATION IMAGING METHOD AND SYSTEM

(71) Applicant: NuCare Medical Systems, Inc., Incheon (KR)

(72) Inventor: Jinhun Joung, Incheon (KR)

(73) Assignee: NUCARE MEDICAL SYSTEMS, INC., Incheon (KR)

( * ) Notice: Subject to any disclaimer, the term of this patent is extended or adjusted under 35 U.S.C. 154(b) by 216 days.

(21) Appl. No.: 14/861,384

(22) Filed: Sep. 22, 2015

(65) Prior Publication Data

US 2017/0031034 A1   Feb. 2, 2017

(30) Foreign Application Priority Data

Jul. 31, 2015   (KR) .................. 10-2015-0108889

(51) Int. Cl.
   *G01T 1/20*      (2006.01)
   *G06T 19/00*     (2011.01)
   *A61B 6/00*      (2006.01)
   *G01N 23/04*     (2018.01)

(52) U.S. Cl.
   CPC .............. *G06T 19/006* (2013.01); *A61B 6/00* (2013.01); *G01N 23/04* (2013.01)

(58) Field of Classification Search
   CPC .......... G06T 19/006; A61B 6/00; G01N 23/04
   USPC ........................................ 250/362
   See application file for complete search history.

(56) References Cited

U.S. PATENT DOCUMENTS

| | | | | |
|---|---|---|---|---|
| 4,429,227 A | * | 1/1984 | DiBianca | G01T 1/1644 250/367 |
| 4,453,075 A | * | 6/1984 | Mattsson | A61B 6/4057 250/363.02 |
| 4,476,385 A | * | 10/1984 | Wunderlich | G01T 1/1648 250/303 |
| 5,986,263 A | * | 11/1999 | Hiroi | H01J 37/28 250/307 |
| 8,243,874 B2 | * | 8/2012 | Carmi | G01T 1/1644 250/366 |
| 2008/0116388 A1 | * | 5/2008 | Joshi | G01T 1/2018 250/370.15 |

(Continued)

OTHER PUBLICATIONS

Redus et al., "A Combined Video and Gamma Ray Imaging System for Robots in Nuclear Environments," Nuclear Instruments and Methods in Physics Research, Dec. 1994, 324-327, Section A 353, N.H. Elsevier, Ann Arbor, MI, United States.

(Continued)

*Primary Examiner* — David Porta
*Assistant Examiner* — Abra Fein
(74) *Attorney, Agent, or Firm* — Levenfeld Pearlstein, LLC

(57) ABSTRACT

A method and a system for preparing a radiation image of a target are provided. The radiation imaging method includes the steps of collecting radiation emission data from a target, classifying the data into at least one energy range, separating the data in each energy range into N independent radiation distributions, processing the data in each of the N independent radiation distributions to estimate its true distribution; and reconstructing a radiation distribution image of the target using the processed data. The system includes at least one radiation detector module and at least one computerized component configured to perform the steps of the method.

26 Claims, 11 Drawing Sheets

(56) References Cited

U.S. PATENT DOCUMENTS

| | | | | |
|---|---|---|---|---|
| 2008/0302967 | A1* | 12/2008 | Klann | G01T 7/00 250/336.1 |
| 2009/0084960 | A1* | 4/2009 | Green | G01T 1/24 250/361 R |
| 2010/0193697 | A1* | 8/2010 | Bal | G01T 1/247 250/370.09 |
| 2011/0299071 | A1* | 12/2011 | Treado | G01N 21/64 356/301 |
| 2012/0108958 | A1* | 5/2012 | Jackson | A61N 5/10 600/427 |
| 2015/0097126 | A1* | 4/2015 | McCord | G01B 11/27 250/492.2 |

OTHER PUBLICATIONS

Guru et al., "A Portable Gamma Camera for Radiation Monitoring," IEEE Transactions on Nuclear Science, Aug. 1995, 940-945, vol. 42, The University of Michigan, Ann Arbor, MI, United States.

"GamaCam Radiation Imaging System," Innovation Technology Summary Report, Feb. 1998, 1-35, vol. 29 Issue 42, U.S. Department of Energy, Washington, DC., United States.

Gal et al., "Operation of the Cartogam Portable Gamma Camera in a Photon-Counting Mode," IEEE Transactions on Nuclear Science, Aug. 2001, 1198-1204, vol. 48, Issue 4, IEEE, United States.

Lee et al., "A Radiation Monitoring System with Capability of Gamma Imaging and Estimation of Exposure Dose Rate," IEEE Transactions on Nuclear Science, Jun. 2002, 1547-1551, vol. 49, No. 3, IEEE, United States.

Yamamura et al., "Development of Three-Dimentional Gamma Camera with Imaging Plates and Multi-Pinhole Collimators," Nuclear Instruments and Methods in Physics Research, Jun. 2003, 577-581, Section A 505, N.H. Elsevier, Japan.

Gmar et al., "Development of Coded-Aperature Imaging With a Compact Gamma Camera," IEEE Transactions on Nuclear Science, Aug. 2004, 1682-1687, vol. 51, No. 4, IEEE, United States.

Potapov et al., "A Gamma Locator for Remote Radioactivity Mapping and Dose Rate Control," Nuclear Science Symposium Conference Record, Oct. 2004, 1551-1555, vol. 3, IEEE, Italy.

Woodring et all, "Advanced Multi-Dimensional Imaging of Gamma-Ray Radiation," Nuclear Instruments and Methods in Physics Research, Jun. 2003, 415-419, vol. 505, Issues 1-2, N.H. Elsevier, United States.

Christian et al., "Portable Video/Gamma Camera for Surveillance, Safeguards, Treaty Verification and Area Monitoring," Institute of Nuclear Materials Management 45th Annual Meeting Presentation, Jul. 2004, 1-8, Radiation Monitoring Devices, Inc., Watertown, MA, United States.

Li et al., "Design of Wide Energy Range Coded Aperature Mask of an Environment Radiation Monitoring System," 2007 IEEE Nuclear Science Symposium Conference Record, Nov. 2007, 1299-1303, vol. 2, IEEE, Honolulu, HI, United States.

Carrel et al., "GAMPIX: a New Gamma Imaging System for Radiological Safety and Homeland Security Purposes," 2011 IEEE Nuclear Science Symposium Conference Record, Oct. 2011, 4739-4744, IEEE, Valencia, Spain.

Gmar et al., "GAMPIX: a New Generation of Gamma Camera," Nuclear Instruments and Methods in Physics Research, Sep. 2010, 638-640, Section A 652, Elsevier, France.

Jan et al., "GATE: a Simulation Toolkit for PET and SPECT," Physics in Medicine and Biology, 2004, 4543-4561, vol. 19, Institute of Physics Publishing, United Kingdom.

Rasmussen, "The Infinite Gaussian Mixture Model," Advances in Neural Information Processing Systems 12, 2000, 554-560, MIT Press, United States.

Reynolds et al., "Robust Text-Independent Speaker Identification Using Gaussian Mixture Speaker Models," IEEE Transactions on Speech and Audio Processing, Jan. 1995, 72-83, vol. 3, Issue 1, IEEE, United States.

Moon, "The Expectation-Maximization Algorithm," IEEE Signal Processing Magazine, Nov. 1996, 47-60, IEEE, United States.

Xuan et al., "EM Algorithms of Gaussian Mixture Model and Hidden Markov Model," 2001 International Conference Proceedings, 2001, 145-148, vol. 1, IEEE, Thessaloniki, Greece.

Bae et al., "Novel Positioning Method Using Gaussian Mixture Model for a Monolithic Scintillator-based Detector in Positron Emission Tomography," Optical Engineering, Sep. 2011, 093606-093606-7, vol. 50, Issue 9, American Institute of Physics, United States.

Shepp et al., "Maximum Likelihood Reconstruction for Emission Tomography," IEEE Transactions on Medical Imaging, Oct. 1982, 113-122, vol. 1, Issue 2, IEEE, United States.

Ollinger, "Maximum-Likelihood Reconstruction of Transmission Images in Emission Computed Tomography via the EM Algorithm," IEEE Transactions on Medical Imaging, Mar. 1994, 89-101, vol. 13, Issue 1, IEEE, United States.

Lange et al., "A Theoretical Study of Some Maximum Likelihood Algorithms for Emission and Transmission Tomography," IEEE Transactions on Medical Imaging, Jun. 1987, 106-114, vol. 6, Issue 2, IEEE, United States.

Kontaxakis et al., "Maximum Likelihood Algorithms for Image Reconstruction in Positron Emission Tomography," Radionuclides for Oncology, Jun. 1998, 73-106, Mediterra Publishers, Athens, Greece.

Aarsvold, Emission Tomography the Fundamentals of PET and SPECT, 2004, v-576, Elsevier Academic Press, London, United Kingdom.

* cited by examiner

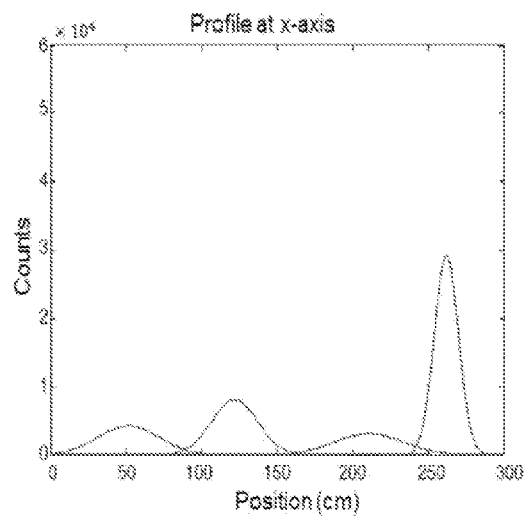
FIG. 7(A)
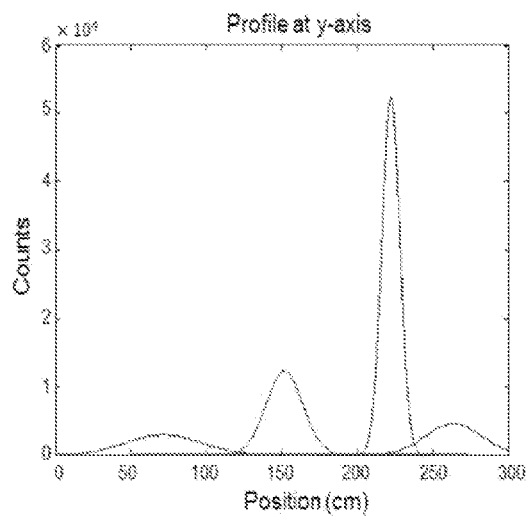
FIG. 7(B)
FIG. 8
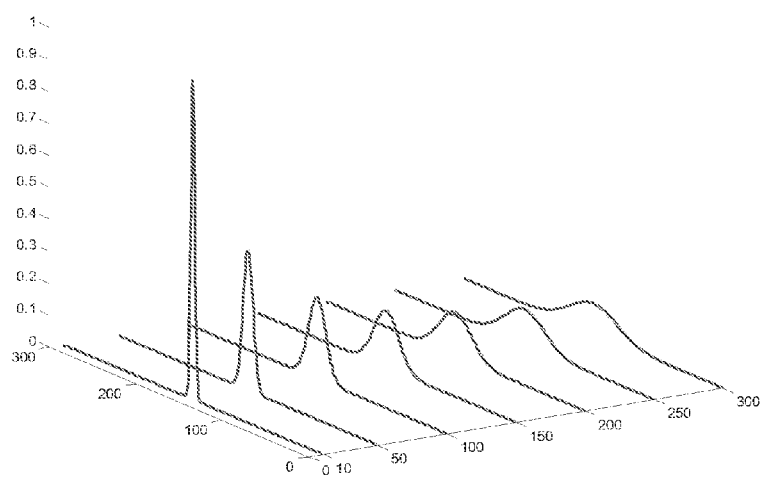

RADIATION IMAGING METHOD AND SYSTEM

CROSS-REFERENCE TO RELATED APPLICATION DATA

This application claims the benefit of priority of Korean Patent Application No. 10-2015-0108889, filed Jul. 31, 2015 entitled, "RADIATION IMAGING METHOD AND SYSTEM".

BACKGROUND OF THE INVENTION

The present disclosure relates to methods and systems for imaging gamma ray emission in a space, and more particularly, two and/or three dimensional gamma ray emission image reconstruction methods and applications thereof.

Radiation imaging techniques have been widely used in the field of diagnostic and therapeutic medical imaging. Among such techniques, nuclear medicine imaging involves imaging of a distribution of gamma ray sources, which are emitted from within a body. In nuclear medicine imaging, radiopharmaceuticals (i.e., gamma ray sources) are taken internally, for example, intravenously or orally, and external detectors are used to capture radiation emitted by the radiopharmaceuticals and to provide images. This method is distinguishable from diagnostic X-raying, wherein external radiation is passed through a body to form an image. Therefore, the nuclear medicine imaging is also referred to as an "emission imaging."

Efforts have been made to utilize emission imaging techniques used in nuclear medicine to image radiation distributions in environment, for example, power plant monitoring, radiation waste management, cargo inspection, radiation contamination monitoring, environmental monitoring, etc.

One of the early research in this area was conducted by R. Redus, et. al. (see Reference 1 in References section below.) Redus et al. disclose a prototype imager, which combines a gamma ray imaging system with a conventional video camera, a personal computer-based data acquisition, and a display system. The gamma ray imager is based on a position sensitive photomultiplier tube (PSPMT) coupled to a segmented scintillator and collimator. The system superimposes a gamma ray image of a radioactivity distribution with a video image of the area, allowing a rapid and intuitive determination of a source location. This research led to a commercialization of "RadScan" series products by RMD instruments, LLC (MA, USA).

Other similar research includes "A portable gamma camera for radiation monitoring" by S. Gure et al. (see Reference 2 in References section below), which discloses a use of a multi-pinhole collimator; "Operations of the CARTOGAM portable gamma camera in a photon counting mode" (see Reference 4 in References section below); and "Development of coded-aperture imaging with a compact gamma camera" (see Reference 7 in Reference section below), which discloses a use of CCD based gamma detector and coded aperture collimator.

Other commercially available products for imaging radiological environment include "GammaCam™" from US Department of Energy (see Reference 3 in References section below) and "RadScan® 800" by BIL Solutions Ltd. (UK).

However, the proposed prior art methods and commercial products have not been widely accepted for imaging radiological environment because of some critical limitations.

Although the principle is similar, the conditions for imaging radiological environment are quite different from that of imaging a human in nuclear medicine. For example, environment imaging covers a much broader area and a distance between a target and a detector is substantially longer when compared to imaging a person. Typically, environment imaging is performed using a detector, which is placed few tens of meters to few meters away from a target. Further, gamma energy measurements in radiological environment imaging range up to few MeV (1,000,000 electron volt). On the other hand, a detector in nuclear medicine is configured to scan close to a contour of a human body and capture gamma rays ranging up to few hundreds of keV (1,000 electron volt.)

Due to such different imaging conditions, prior art environment imaging systems, which were based on nuclear medicine technologies for human imaging, posed some fundamental limitations, such as inferior sensitivity and spatial resolution. There are several factors that affect sensitivity of environment imaging systems:

Imaging a wide area from a long distance: sensitivity is inversely proportional to a distance square as shown in equation (1), where d is a distance between a detector and a radiation source/target. Thus, a long distance between a detector and a target is one of the major factors that cause a decrease in sensitivity of a detector system for radiological environment imaging.

$$\text{sensitivity} \approx \frac{1}{d^2} \quad (1)$$

Pinhole type collimation: a collimator is a necessary component for gamma emission imaging. It classifies directions of incoming gamma rays. However, in radiological environment imaging, where a relatively small gamma detector is used to cover a wide target area, pinhole or coded aperture type collimators are often used, which also contribute to decrease in the sensitivity of a detector system. Further, a heavier and thicker collimation required for higher energy gamma ray measurements in radiological environment also causes a sensitivity drop.

A scintillator is another essential component in a gamma imaging system, which converts gamma ray into visible photons. In order to sufficiently block incoming gamma ray, absorb their energy, and scintillate, a thickness of a scintillator should be configured according to an amount of incoming gamma ray energy. As such, a substantially thicker scintillator is required for a system for environment imaging, which measures substantially higher energy gamma ray compared to systems for nuclear medicine. However, the thickness of a scintillator is inversely related to an intrinsic spatial resolution in conventional gamma imaging systems. Thus, the thickness of scintillator may not be increased freely due to the spatial resolution trade off.

Further, there are several factors that affect spatial resolution of environment imaging systems:

Imaging a long distance target: the spatial resolution of an imaging system is linearly proportional to a distance as shown in equation (2) where d is a distance between a detector and a radiation source. Thus, as a distance between a detector and a source increases, the resolution of an imaging system degrades.

$$\text{resolution} \approx d \quad (2)$$

Penetration: some portions of incoming gamma ray penetrate through a collimator shielding, especially around opening edges of a pinhole or coded aperture holes. Such penetration of gamma ray increases as incoming gamma ray energy increases. Thus, a decrease in spatial resolution due to gamma ray penetration is more significant in environment imaging systems, which involve higher energy gamma ray.

Thickness of scintillator: as discussed above, a thicker scintillator may improve sensitivity of an imaging system. However, thicker the scintillator, broader is the detector response function, which leads to resolution degradation.

Since the sensitivity and resolution are conflicting parameters in a gamma ray imaging system, it is difficult to improve both parameters simultaneously. Consequently, no practical solution has been proposed from numerous previous attempts to develop methods and systems for the field of radiological environment imaging.

REFERENCES

1. "A combined video and gamma ray imaging system for robots in nuclear environments", R. Redus, M. Squillante, J Gorden, G Knoll and D. Wehe, Nuclear Instruments and Methods in Physics Research A 353 (1994) 324-327
2. "A portable gamma camera for radiation monitoring", S. Guru, Z. Hee, D. Wehe and G. Knoll, IEEE Transactions on Nuclear Science, (1995) 367-370
3. "GammaCam radiation imaging system". Deactivation and decommissioning focus area. Department of Energy. 1998.
4. "Operation of the CARTOGAM portable gamma camera in a photon-counting mode", O. Gal, B. Dessus, F. Jean, F Laine and C. Leveque., IEEE Transactions on Nuclear Scinecne. Vol 48, No 4, 2001.
5. "A radiation monitoring system with capability of gamma imaging and estimation of exposure dose rate", W. Lee, G. Cho and H. Kim, IEEE Transactions on Nuclear Science, V49, N3 (2002) 1547-1551
6. "Development of three-dimensional gamma camera with imaging plates and multi-pinhole collimators", N. Yamamura, A. Uritani, K. Watanabe, J. Kawarabayashi, T. Lguchi., Nuclear Instruments & Methods in Physics Research A. 505 (2003) 577-581
7. "Development of coded-aperture imaging with a compact gamma camera", M. Gmar, O. Gal, C. Goaller, O. Ivanov, V. Potapov, V. Stepanov, F. Laine, F. Lamadie., IEEE NSS MIC 2004.
8. "A gamma locator for remote radioactivity mapping and dose rate control", V. Potapov, N. Kononov, O. Ivanov, S. Ignatov, V. Stepanov, A. Chesnokov and V. Volkov., IEEE NSS MIC, 2004.
9. "Advanced multi-dimensional imaging of gamma-ray radiation", M. Woodring, D. Beddingfield, D. Souza, G. Entine, M. Squillante, J. Christian and A. Kogan. Computer Physics Communications,
10. "Portable Video/Gamma Camera for surveillance, safeguards, treaty verification and area monitoring, J. Christian, M Squillante, M. Woodring and G Entine., INMM meeting in Orlando Fla., 2004.
11. "Design of wide energy range coded aperture mask of an environment radiation monitoring system", X. Li, Z. Wu, Y. Liu, T. Ma and Y. Jin., IEEE Nuclear Science Symposium Conference Record, 2007.
12. "GAMPIX: a new gamma imaging system for radiological safety and homeland security purposes", F. Carrel and et. Al., IEEE NSS MIC 2011.
13. "GAMPIX: a generation of gamma camera", M. Gmar, M. Agelou. F. Carrel and V. Schoepff., Nuclear Instruments and Methods in Physics Research A. 652 (2011), 638-640.
14. "GATE: a simulation toolkit for PET and SPECT." Jan, S., et al. *Physics in medicine and biology* 49.19 (2004): 4543.
15. "The infinite Gaussian mixture model." Rasmussen, Carl Edward. *NIPS. Vol.* 12. 1999.
16. "Robust text-independent speaker identification using Gaussian mixture speaker models." Reynolds, Douglas A., and Richard C. Rose. *Speech and Audio Processing, IEEE Transactions on* 3.1 (1995): 72-83.
17. "The expectation-maximization algorithm." Moon, Todd K. *Signal processing magazine, IEEE* 13.6 (1996): 47-60.
18. "EM algorithms of Gaussian mixture model and hidden Markov model." Xuan, Guorong, Wei Zhang, and Peiqi Chai. *Image Processing, 2001. Proceedings. 2001 International Conference on. Vol.* 1. IEEE, 2001.
19. "Novel positioning method using Gaussian mixture model for a monolithic scintillator-based detector in positron emission tomography." S. Bae, K. Lee, C. Seo, J. Kim, S. Joo and J. Joung. *Optical Engineering* 50.9 (2011): 093606-093606.
20. "Maximum likelihood reconstruction for emission tomography." Shepp, Lawrence A., and Yehuda Vardi. *Medical Imaging, IEEE Transactions on* 1.2 (1982): 113-122.
21. "Maximum-likelihood reconstruction of transmission images in emission computed tomography via the EM algorithm." Ollinger, John M. *Medical Imaging, IEEE Transactions on* 13.1 (1994): 89-101.
22. "A theoretical study of some maximum likelihood algorithms for emission and transmission tomography." Lange, Kenneth, Mark Bahn, and Roderick Little. *Medical Imaging, IEEE Transactions on* 6.2 (1987): 106-114.
23. "Maximum likelihood algorithms for image reconstruction in positron emission tomography." Kontaxakis, George, and Ludwig G. Strauss. *Mediterra, Athens* (1998).
24. *"Emission tomography: the fundamentals of PET and SPECT"*. Wernick, Miles N., and John N. Aarsvold. Academic Press, 2004.

BRIEF SUMMARY OF THE INVENTION

The present disclosure provides various embodiments of a radiation imaging method and a system that address the sensitivity and resolution problems in prior arts. The method enables simple and cost effective system designs to provide imaging systems that may be optimized for various applications in the field of radiological environmental imaging. Two dimensional and three dimensional gamma ray emission image reconstruction methods and applications thereof for stationary radioactive sources in three dimensional (3D) spaces or in moving objects are provided. In an embodiment, a radiation imaging method may provide a two or three dimensional illustrative representation of a gamma ray distribution. Further, the imaging method may also provide quantitative activity concentration and spectroscopic information for each of gamma sources in a target environment.

In one aspect, a method for imaging a "hot spot"-like radioactive source distribution in a target environment is provided according to various embodiments. Such an imaging method is also referred to as "hot-spot imaging" in the present disclosure. During research and development of the present disclosure, it was discovered that the essential components and parameters for prior art imaging detectors, such as a collimator, intrinsic spatial resolution, and sampling requirements, are no longer essential in the "hot-spot imaging." This surprising discovery made it possible to develop imaging methods and systems that deviate from the known requirements of prior art gamma ray imaging methods and systems. Accordingly, an imaging method requiring substantially less sampling/measurements, for which a simplified detector configured for "hot-spot imaging" may be used, is provided according to various embodiments.

In an embodiment, a method for 3D image reconstruction includes the step of acquiring two 2-dimensional (2D) projections, which may be measured at 90° apart, i.e., orthogonal to each other. In another embodiment, an imaging detector, which provides a sensitivity gain of about 4 orders of magnitude ($10^4$) compared to that of a prior art pinhole type detector is provided.

In another aspect, a radiation imaging method including the steps of collecting radiation emission data from a target, classifying the data into at least one energy range, separating the data into N independent radiation distributions, processing the data to recover resolution, and reconstructing a radiation distribution image of the target using the processed data is provided. The radiation emission data may be collected by measuring the target including at least one radiation source by at least two projections. In the step of separating the data, the data in each energy range is separated into N independent radiation distributions, where N is a number of the radiation sources, and each of the N independent radiation distributions corresponds to each of the radiation sources. The data in each of the N independent radiation distribution is processed to estimate its true distribution, and the radiation distribution image is reconstructed using the corrected or process data.

In an embodiment, the data may be classified into a plurality of energy ranges. In such an embodiment, the method further includes the step of consolidating the radiation distribution images prepared from each of the plurality of energy ranges and providing quantitative information including activity concentration and spectroscopic information.

The at least two projections may be measured using a radiation detector module comprising a collimator, a scintillator, and a photo-sensor. In one embodiment, the collimator may be a flat field collimator having an opening diameter about 25 mm to about 76 mm, and the scintillator has a thickness of about 25 mm to about 127 mm. In another embodiment, the radiation detector module may be an imaging detector having an n×m array intrinsic spatial resolution.

In another embodiment, the radiation detector module may collect projections from at least one view angle by raster scan, linear motion, tilting and/or rotating. In yet another embodiment, the at least two projections may be measured using an array of detector modules.

The step of separating the data into N independent radiation distributions may include approximating the data in each of the energy ranges as a Gaussian mixture of N independent Gaussian distributions according to the equation:

$$P(x) = \sum_{n=1}^{N} \pi_n N(x \mid \mu_n, \Sigma_n)$$

wherein $x=(x^1, x^2, \ldots, x^d)$ for d dimension and mixing coefficient $\pi_n$ is denoted weight of each component Gaussian distribution, which satisfies an equation:

$$\sum_{n=1}^{N} \pi_n = 1$$

wherein each component $N(x|\mu_n,\Sigma_n)$ is multivariate Gaussian distribution:

$$N(x \mid \mu_n, \Sigma_n) = \frac{1}{(2\pi|\Sigma_n|)^{1/2}} e^{-\frac{1}{2}(x-\mu_n)^T \Sigma_n^{-1}(x-\mu_n)}$$

wherein $\mu_n, \Sigma_n$ are marked mean and covariance of Gaussian distribution; and
finding a solution that maximize the equation:

$$\ln\{p(X)\} = \sum_{m=1}^{M} \ln p(x_m) = \sum_{m=1}^{M} \ln\left\{\sum_{n=1}^{N} \pi_n N(x_m \mid \mu_n, \Sigma_n)\right\}$$

wherein, the parameters $\pi_n, \mu_n, \Sigma_n$ are calculated using an expectation maximization method.

In an embodiment, the step of processing the data to recover resolution may be performed using a point spread function, which may be empirically measured or estimated by a simulation method. In another embodiment, the step of processing the data to recover resolution may be performed using a transfer function.

The step of processing the data in each of the N independent radiation distributions to recover resolution may include calculating a deconvolution between each of the projections and a point spread function by solving an equation:

$$T(x) = \sum_{n=1}^{N} \{decon(P_n(x), psf_n(x))\}$$

wherein, $T_n(x)$ is a true response function and $psf_n(x)$ is a point spread function corresponding to a distance of a radiation source of $T_n(x)$, and $P_n(x)$ is a separated $n^{th}$ Gaussian profile of a projection. The step of processing the data may also recover a shape and intensity of each of the radiation sources. In another embodiment, the point spread function may be replaced with transfer function of a given system.

In an embodiment, the step of reconstructing a radiation distribution image may use a maximum likelihood expectation maximization based reconstruction algorithm. In another embodiment, the step of reconstructing a radiation distribution image may use a statistics based reconstruction algorithm.

In another embodiment, the step of reconstructing a radiation distribution image may provide quantitative activity concentration and spectroscopic information of each distributions.

In some embodiments, the step of reconstructing a radiation distribution, the reconstructed radiation image may be superimposed with video image. Further the superimposed image may be visually presented by virtual reality methods.

In yet another aspect, a system for preparing a radiation image of a target is provided. The system includes at least one radiation detector module for collecting radiation emission data from a target. The target may be a two-dimensional space or a three-dimensional space including at least one stationary radiation source. The radiation emission data may include measurements from at least two projections, which may be measured from at least two different angle using raster, linear, tilting, or rotating scan.

The system also includes at least one computerized component configured for classifying the data into at least one energy range, separating the data in each energy range into N independent radiation distributions, where N is a number of radiation sources in the target and each of the N independent radiation distributions corresponds to each of the radiation sources, processing the data in each of the N independent radiation distributions to recover resolution, and reconstructing a radiation distribution image of a target using the processed data.

In an embodiment, the system may include two detector modules. Such a system may be used to prepare a radiation image of a three dimensional space including at least one stationary radiation source, in which the two detector modules are configure to measure radiation emission from the at least one stationary radiation source.

In another embodiment, the target may be a moving object. In such an embodiment, the system may comprise two arrays of stationary radiation detector modules including a first array arranged parallel to a z-axis and a second array arranged parallel to a y-axis. The two arrays of stationary radiation detector modules may be configured to measure radiation emission data of the target as the target moves through the two arrays of stationary radiation detector modules in an x-axis direction.

In yet another embodiment, the at least one radiation detector module may be configured to scan the target in a first path along an x-axis to obtain measurements for an x-z plain. Subsequently the target is rotated by 90°, and the at least one radiation detector module may scan a second path along the x-axis to obtain measurement for a y-z plain.

In some embodiments, the at least one radiation detector module may comprise a radiation detector module including a flat field collimator, a scintillator and a photo-sensor, in which the flat field collimator may include an opening having a diameter of about 25 mm to about 76 mm, and the scintillator may have a thickness of about 25 mm to about 127 mm.

Other aspects, objectives and advantages of the invention will become more apparent from the following detailed description when taken in conjunction with the accompanying drawings.

BRIEF DESCRIPTION OF THE DRAWINGS

The benefits and advantages of the present embodiments will become more readily apparent to those of ordinary skill in the relevant art after reviewing the following detailed description and accompanying drawings, wherein:

FIG. 7(A) is a graph of the x-axis projection measurements of FIG. 6(A) after the projection separation step ST30 of FIG. 1;

FIG. 7(B) is a graph of the y-axis projection measurements of FIG. 6(B) after the step of projection separation ST30 of FIG. 1;

FIG. 8 is a graph of a point spread function according to an embodiment;

DETAILED DESCRIPTION OF THE INVENTION

Figure 1:
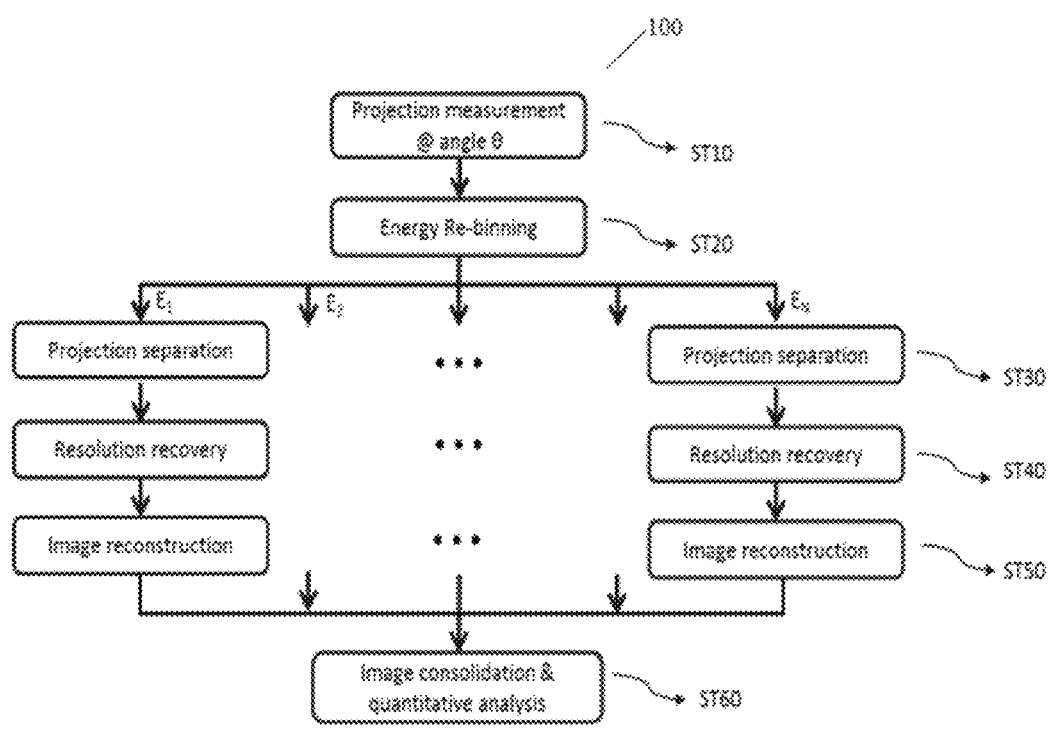
FIG. 1 is a flow chart including the steps of a radiation imaging method according to an embodiment.

While the present disclosure is susceptible of embodiment in various forms, there is shown in the drawings and will hereinafter be described a presently preferred embodiment with the understanding that the present disclosure is to be considered an exemplification and is not intended to limit the disclosure to the specific embodiment illustrated.

Referring to FIG. 1, the steps of a radiation imaging method according to an embodiment are provided in a flow chart. The method generally includes the steps of measuring a target space to obtain projection measurements, re-binning and signal processing of the projection measurements, and constructing an image using the processed projection measurements. The projection measurements are also referred to as a "projection set" in the present disclosure.

Figure 2:
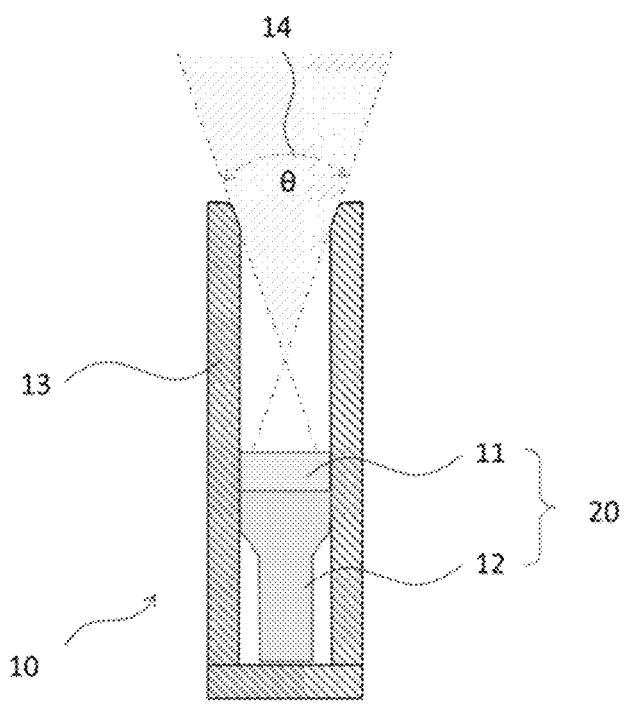
FIG. 2 is a schematic illustration of a detector module according to an embodiment.

FIG. 2 is an illustration of a detector module 10 according to an embodiment. The detector module 10 generally includes a collimator 13 and a radiation detector 20 comprising a scintillator 11 and a photo-sensor 12. In an embodiment, the collimator 13 may be a flat field collimator, and the scintillator 11 is optically coupled to the photo-sensor 12.

A typical collimator in prior art imaging detectors is configured to include functions for selectively accepting incoming gamma rays and identifying their direction. The collimator 13 need not be configured for such functions. Rather, the collimator 13 of the detector module 10 may be configured for shielding and confining a field of view 14 of the radiation detector 20. Further, the detector module 10 need not be configured as a prior art imaging detector having an n×m array intrinsic spatial resolution. As such, the photo-sensor 12 may be configured as a radiation counting detector with spectroscopic capability. Thus, the detector module 10 may be constructed to have a relatively simple configuration, yet providing improved sensitivity, which is also cost-effective.

In an embodiment, the detector module 10 is used for projection measurements in the imaging method 100 of FIG. 1. However, other radiation detectors and imaging modules including a collimator may also be used for the imaging method 100 of FIG. 1.

Figure 3:
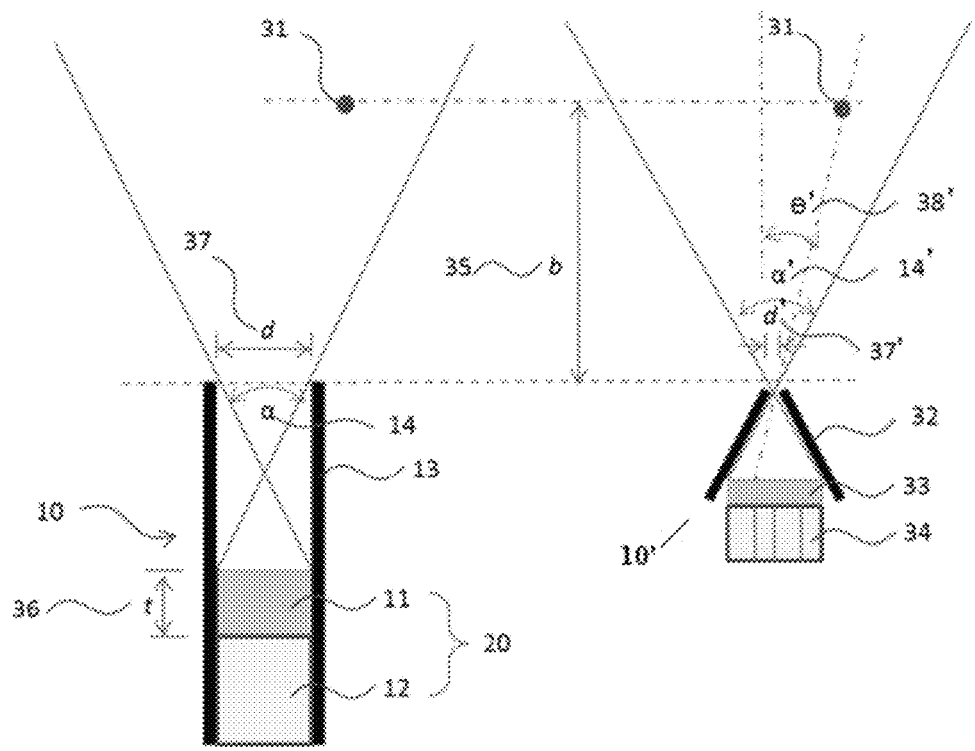
FIG. 3 is a schematic illustration comparing the detector module of FIG. 2 and a prior art pinhole detector.

In FIG. 3, the detector module 10 and a prior art pinhole-type detector 10' are illustrated side by side to explain the differences between the two detectors. A point radiation source 31 is detected by each of the detectors 10, 10' via an opening hole having a diameter (d, d') 37, 37' by traveling a distance (b) 35, wherein α, α' is an acceptance angle 14, 14', θ' is an incidence angle to the normal 38', and t is a thickness 36 of the scintillator 11. The prior art detector 10' including a pinhole collimator 32, and a pixelated scintillator 33 couple to PS-PMT 34 is the most common form of a detector configuration used in prior art radiological environmental imaging.

A sensitivity gain achieved by using the detector module 10 may be explained by equation (3). The system sensitivity is a product of collimator sensitivity and detector efficiency:

$$S_e = C_e \times D_e \quad (3)$$

where $S_e$, $C_e$ and $D_e$ are system sensitivity, collimator sensitivity and detector efficiency, respectively. $C_e$ and $D_e$ may be derived from following equations.

$$C_e \approx \frac{d_e \cos^2 \theta}{16b^2} \quad (4)$$

$$d_e = \sqrt{d[d + 2\mu^{-1}\tan(\alpha/2)]} \quad (5)$$

$$D_e = g_e m_e \quad (6)$$

$$g_e \approx \frac{d^2}{b^2}, m_e = 1 - e^{-\mu t} \quad (7)$$

where, d, $d_e$, $g_e$ and $m_e$ is a hole diameter, hole diameter & incident angle efficiency, geometric efficiency (i.e., solid angle) and photons absorption fraction, respectively.

For example, considering that a typical hole diameter 37' for a prior art pinhole-type collimator 32 is about 4 mm, while the opening diameter 37 of the collimator 13 of the detector module 10 is about 50 mm for most practical applications, the sensitivity gain from using the detector module 10 over using the prior art pinhole-type detector module 10' may be about 4 orders of magnitude ($10^4$) based on the equation (4, 5, 6, 7).

Further sensitivity improvement may be achieved by employing a thicker scintillator 11, thereby enhancing stopping power of incoming radiation within the scintillator 11. The thickness (t) 36 of the scintillator 11 is shown in FIG. 3. In high energy imaging, the thickness 36 of the scintillator 11 becomes a more significant factor for photon absorption within the scintillator 11.

A hole diameter 37' of a typical collimator in prior art imaging detectors is about 1 mm to about 6 mm. The collimator 13 of the detector module 10 may be configured with a substantially larger opening diameter. For example, the collimator 13 may be a flat field collimator having an opening diameter 37 of about 25 mm to about 76 mm (3 inches). In an embodiment, a detector module 10 may include a flat field collimator 13 having an opening diameter 37 of greater than about 10 mm, for example, about 25 mm (1 inch) to about 76 mm (3 inches), and a scintillator 11 having a thickness 36 of about 25 mm (1 inch) to about 127 mm (5 inches), and a photo sensor 12.

As discussed above, due to the competing sensitivity and spatial resolution parameters in prior art imaging detectors, a significant limitation exists in increasing a thickness of the scintillator 33. In contrast, in the detector module 10, the thickness 36 of the scintillator 11 may be increased without a limitation according to incoming gamma ray energy.

A sensitivity gain achieved by the configuration of the detector module 10 may be explained by the equations (4) to (7). However, since the detector module 10 is not configured as an imaging detector having an intrinsic spatial resolution, the detector module 10 may not be used for conventional imaging methods. The present disclosure provides various embodiments of an imaging method utilizing a non-imaging detector, such as the detector module 10.

Now referring back to FIG. 1, a flow chart including the steps of a radiation imaging method 100 according to an embodiment is provided. The imaging method 100 comprises the steps of: Projection Measurement ST10, Energy Re-binning ST20, Projection Separation ST30, Resolution Recovery ST40, Image Reconstruction ST50, and Image Consolidation & Quantitative analysis ST60.

Figure 4:
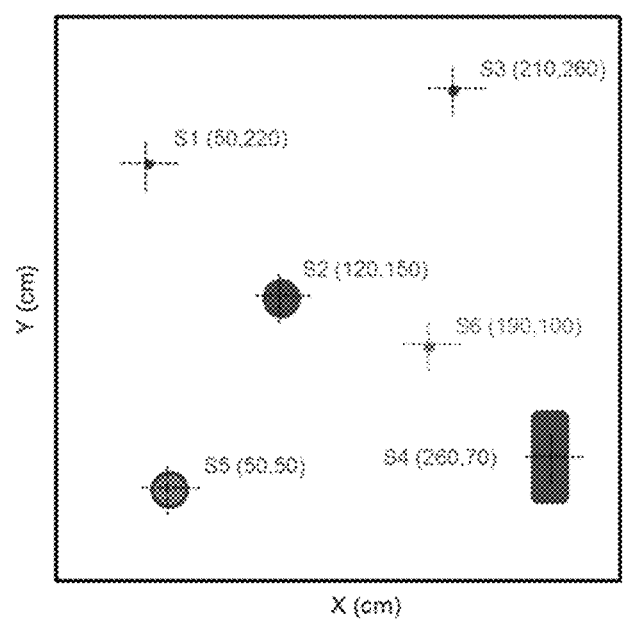
FIG. 4 is an schematic illustration of a sample target imaging space including locations of radiation sources according to an embodiment.

To facilitate understanding of the imaging method 100, exemplary graphs and/or images generated using data from a simulation after each of the steps of FIG. 1 are provided. The simulation was conducted with a GATE simulation tool disclosed in Jan, S., et al. (See above Reference 14.) For simplicity of the simulation, a target imaging space was confined to a 2D space of an area of 3×3 $m^2$ including six "hot spot"-like radioactive sources as illustrated in FIG. 4. The conditions of the simulation are summarized in Table 1.

TABLE 1

Simulation Conditions

| Radioactive Source | Location (x, y) cm | Shape | Radius (cm) | Activity (µCi) | Energy (keV) |
|---|---|---|---|---|---|
| S1 | (50, 220) | sphere | 1 | 300 | 662 |
| S2 | (120, 150) | sphere | 5 | 200 | 662 |
| S3 | (210, 260) | sphere | 1 | 300 | 662 |
| S4 | (260, 70) | cylinder | 5 × 20 | 400 | 662 |
| S5 | (50, 50) | sphere | 5 | 600 | 332 |
| S6 | (190, 100) | sphere | 1 | 200 | 511 |

1. Projection Measurement Step (ST10)

A linear sampling, which is also referred to herein as a "projection", is obtained by superimposing measurements of radiation activity within a 3D imaging space into a 2D plain at a particular angle.

Generally, in a computerized tomography (CT) reconstruction, a detector moves linearly and/or spins around a target object to obtain linear and angular sampling data, wherein the linear sampling interval generally follows the Nyquist sampling theory:

$$\text{linear sampling distance} \leq \frac{1}{2v_{max}} \quad (8)$$

where $v_{max}$ is Nyquist frequency.

An angular sampling interval (an angle between projections) should provide sampling around the periphery of a target object at approximately the same intervals as the linear sampling distance. Thus, if projections are acquired around a field of view of diameter D and the linear sampling distance across each projection is d, the number of angular views should be approximately the length of 180 arc over which projections are taken divided by the sampling distance:

$$\text{Number of angular views} = \frac{\pi D}{2d} \quad (9)$$

In an embodiment, a linear sampling requirement for the step of projection measurement ST10 of the imaging method 100 may also follow the Nyquist theory. However, an angular sampling requirement may be substantially simplified. For example, the angular sampling requirement for a 3D imaging reconstruction may be satisfied to two 2D projections. Preferably, the two projections are taken orthogonal to each other. In other embodiments, the projections may be taken at different angles.

Such a substantial reduction in the angular sampling requirement was made possible only after redefining the environment imaging as "hot-spot imaging."

In an embodiment, a pair of linear projections $P(x_{0°})$ and $P(x_{90°})$ may be collected by scanned along the x-axis (i.e., angle 0°) and y-axis (i.e., angle 90°) of a target imaging space.

2. Energy Re-binning Step (ST20)

Figure 5:
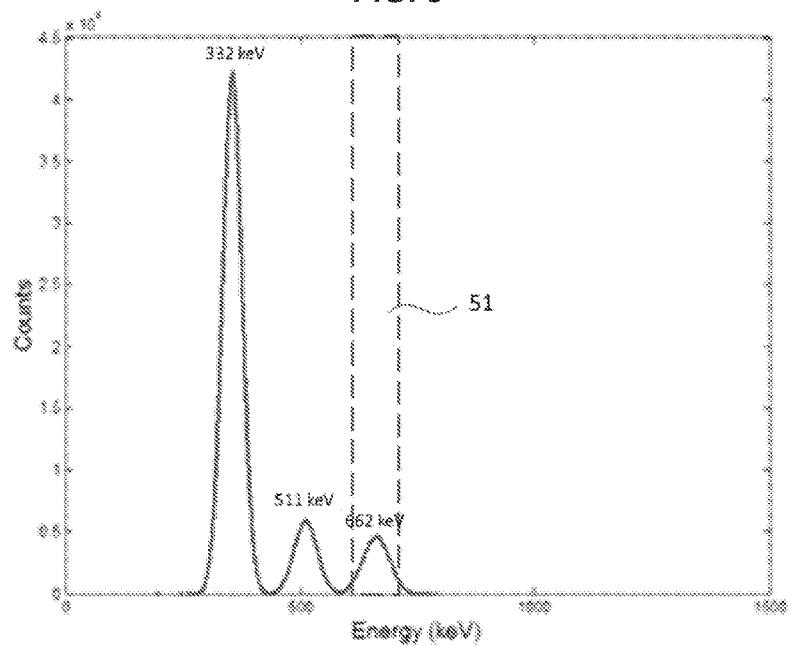
FIG. 5 is a graph of an energy spectrum of gamma rays captured by the detector module of FIG. 2 during a simulation using the radiation sources in the imaging space of FIG. 4.
Figure 6A:
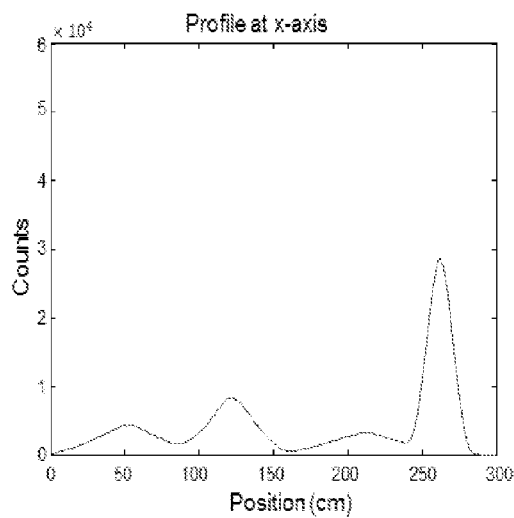
FIG. 6(A) is a graph of x-axis projection measurements from a simulation of the imaging space of FIG. 4 measured using the detector module of FIG. 2 after the energy re-binning step ST20 of FIG. 1.
Figure 6B:
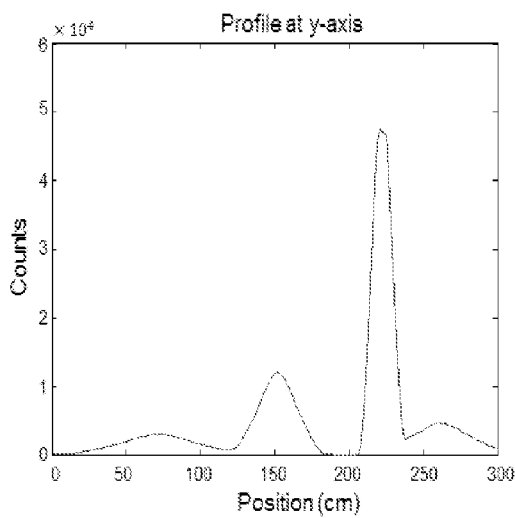
FIG. 6(B) is a graph of a y-axis projection measurements from a simulation of the imaging space of FIG. 4 measured using the detector module of FIG. 2 after the energy re-binning step ST20 of FIG. 1.

Energy re-binning step is classification of a projection set based on its gamma energy. FIG. 5 shows an example of energy spectrum of gamma rays captured by the detector module 10 during a simulation. In an example of the energy re-binning step, the projection of Cs-137 sources having energy of 662 keV photo-peak, may be separated by setting an energy discrimination as shown in FIG. 5 with a dashed box 51, such that only gamma rays within an energy range of 662 keV±10% are binned together. In this example, gamma rays from S1 to S4 sources in the imaging space of FIG. 4 were binned together to provide the projections shown in FIGS. 6(A) and 6(B).

3. Projection Separation Step (ST30)

In the projection separation step, the measured projections are separated into an independent distribution set of individual radioactive source. In the present disclosure, a projection at angle θ, i.e., $P(x_θ)$ was treated as a mixture of multiple Gaussian, and Gaussian separation method was applied to derive N independent Gaussian distributions from it. However, a projection P(x) may be treated as any distribution model and a corresponding method for separating the projection may be applied.

For example, where a projection P(x) includes measurements of N radiation sources, Gaussian mixture of N independent Gaussian distribution is derived as shown in equation (10).

$$P(x) = \sum_{n=1}^{N} \pi_n N(x|\mu_n, \Sigma_n) \quad (10)$$

where $x = (x^1, x^2, \ldots, x^d)$ for d dimension, and mixing coefficient $\pi_n$ is a denoted weight of each component Gaussian distribution and satisfies equation (11).

$$\sum_{n=1}^{N} \pi_n = 1 \quad (1)$$

Each component $N(x|\mu_n, \Sigma_n)$ is multivariate Gaussian distribution.

$$N(x|\mu_n, \Sigma_n) = \frac{1}{(2\pi|\Sigma_n|)^{1/2}} e^{-\frac{1}{2}(x-\mu_n)^T \Sigma_n^{-1} (x-\mu_n)} \quad (12)$$

with $\mu_n, \Sigma_n$ are marked mean and covariance of Gaussian distribution. (See References 15, 16.)

Various methods may be used for separating a profile P(x) into individual distribution corresponding to sources. One of most popular method is the maximum likelihood (ML) algorithm where unknown parameters $\pi_n, \mu_n, \Sigma_n$ in Eq. (12) are estimated by finding values of these parameters that maximize the log likelihood function derived in Eq. (13) below.

$$\ln\{p(X)\} = \sum_{m=1}^{M} \ln p(x_m) = \sum_{m=1}^{M} \ln \{\sum_{n=1}^{N} \pi_n N(x_m|\mu_n, \Sigma_n)\} \quad (13)$$

where M is a vector set of measurement data $\{x_1, \ldots, x_M\}$. In the present disclosure, M is a projection data $P(x_m)$.

If ML does not provide a closed form solution, the parameters $\pi_n, \mu_n, \Sigma_n$ may be calculated using expectation maximization (EM) technique. (See References 17, 18, 19.)

A Gaussian separation example of $P(x_{0°})$ and $P(x_{90°})$ are shown in FIGS. 7(A) and 7(B).

4. Resolution Recovery Step (ST40)

Resolution recovery step is another aspect that clearly distinguishes the imaging method 100 from prior art methods. FIG. 8 shows a set of projections of a point source at different distance. In general, this is referred to as "point spread function (PSF)" or "transfer function" of a given system. The difference of PSF spread is caused by an attenuation of gamma photon traveling different distant before being captured in the detector system. In addition, the point spread function is radiation photon energy dependent as well. Therefore, PSF of a given detector system is function of distance, energy and attenuation. i.e., $$\text{psf} = f\{\text{distance, energy, attenuation}\} \quad (14)$$

In prior art systems and methods, a common approach for correcting such distance dependent PSF is by using an arithmetic or geometric mean of projections obtained at 180° angle to each other. Such a correction method may also be used for the imaging method 100 by collecting additional projections at 180° opposite angle. However, in embodiments wherein a minimized sampling of two orthogonal projections is collected, which enables simplified configuration of imaging systems for various applications, a PSF is empirically measured or estimated by Monte Carlo simulation.

Since a PSF is identical within a 3D space as long as a distance between a point source and a detector remains the same, only one PSF measurement is a necessary condition. i.e., it is a vector set of measurement data psf=$\{m_1, \ldots m_d\}$, where $m_d$ is a psf at a distance d. The variance and sum of $m_d$ represent resolution and attenuation correction factors, respectively.

In practice, a "hot spot"-like gamma source is typically not a point source. Rather, a gamma source is closer to a sphere or elliptical shape. Therefore, a separated $n^{th}$ Gaussian profile of a projection, i.e., $P_n(x)$ is derived as, $$P_n(x) = T_n(x) * psf_n(x) \quad (15)$$

where $T_n(x)$ is a true response function and $psf_n(x)$ is a point spread function corresponding to the distance of a source of $T_n(x)$, and * denotes a convolution operation.

The true distribution T(x) can be derived as, $$T(x) = \Sigma_{n=1}^{N} \{decon(P_n(x), psf_n(x))\} \quad (16)$$

where, $decon(P_n(x), psf_n(x))$ denotes a deconvolution operation between $P_n(x)$ and $psf_n(x)$. Therefore, the resolution recovery step ST40 may be expressed based on an inverse of the equation (15) as provided in equation (17). In the resolution recovery step ST40, resolution and attenuation may be recovered simultaneously.

Figure 9A:
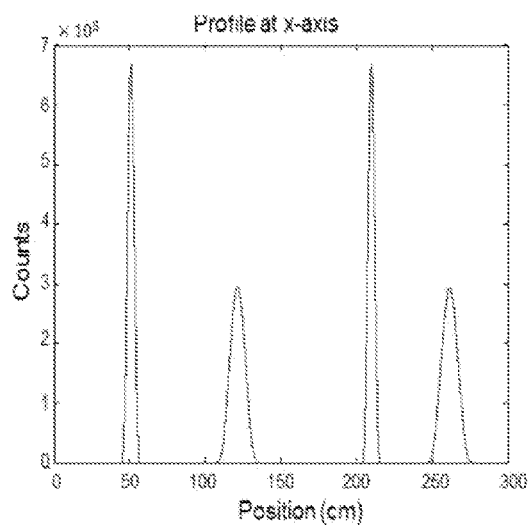
FIG. 9(A) is a graph of the x-axis projection measurements of FIG. 7(A) after the resolution recovery step ST40 of FIG. 1.
Figure 9B:
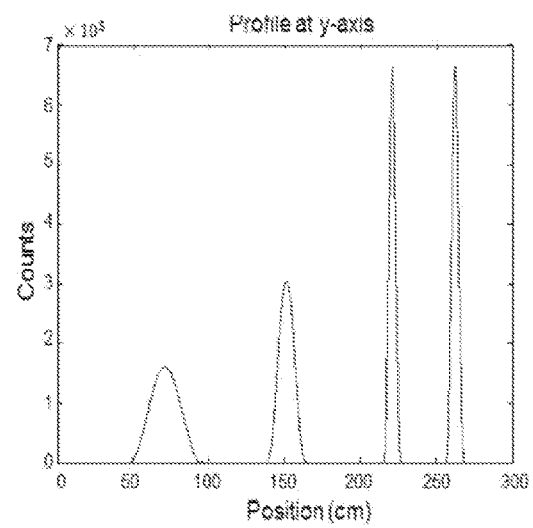
FIG. 9(B) is a graph of the y-axis projection measurements of FIG. 7(B) after the resolution recovery step ST40 of FIG. 1.

Example of final resolution recovered projections $T(x_{0°})$ and $T(x_{90°})$ are shown in FIGS. 9(A) and 9(B).

5. Image Reconstruction Step (ST50)

A reconstruction of an image from an acquired projection profile is an inverse problem. Often, it is not possible to exactly solve an inverse problem directly. In such case, a direct algorithm may be used to approximate a solution, which may cause visible reconstruction artifacts in a reconstructed image.

Alternatively, an iterative algorithm approach may be used, which involves multiple iteration steps and provides an improved reconstruction at a cost of a higher computation time. The advantages of the iterative approach include improved insensitivity to noise and improved capability for reconstruction with incomplete data. The method has been applied in emission tomography modalities like SPECT and PET, where there is significant attenuation along ray paths and noise statistics are relatively poor.

In the image reconstruction step ST50, maximum likelihood expectation maximization (MLEM) method was used to reconstruct an image from an incomplete set of measured data. Details of this algorithm are disclosed in References 20-24. See above References section.

Figure 10:
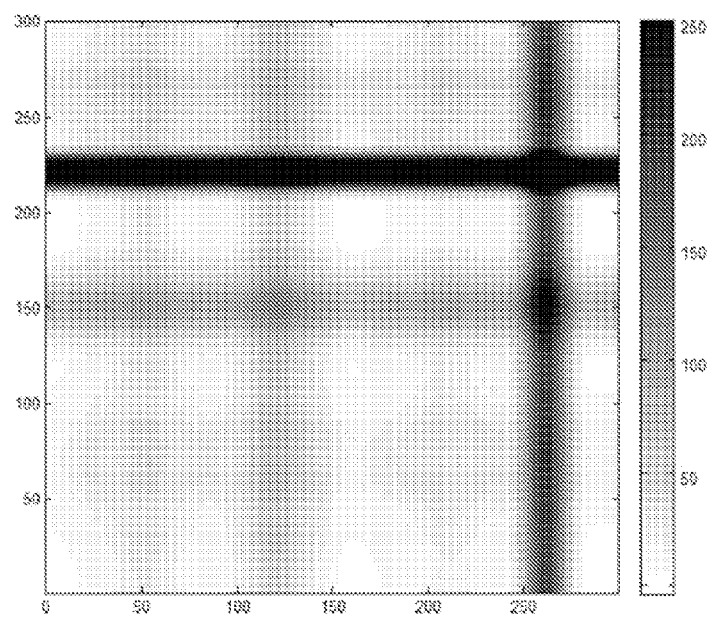
FIG. 10 is a reconstructed 2D image prepared using the uncorrected projections of FIGS. 7(A) and 7(B) using a filter back projection (FBP) method.
Figure 11:
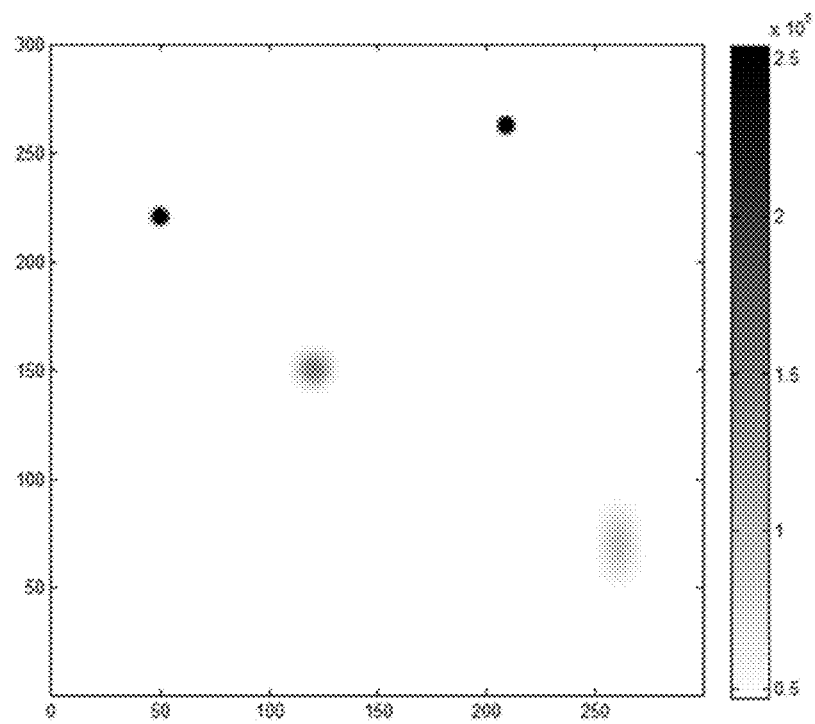
FIG. 11 is a reconstructed 2D image prepared using the corrected projections of FIGS. 9(A) and 9(B) using a maximum likelihood expectation maximization (MLEM) method.

FIG. 10 is an image reconstructed using a prior art filtered back projection (FBP) reconstruction algorithm with uncorrected projections, i.e., P(x). FIG. 11 is an image reconstructed using the MLEM method with resolution recovery applied projections, i.e., T(x). An advantage of the MLEM method in suppressing artifacts caused by incomplete sampling is clearly shown in FIG. 11.

6. Image Consolidation and Quantitative Analysis Step (ST60)

Consolidation of images from different energy bins and quantitative analysis, such as activity concentration and isotope identification are performed in the step 60 (ST60).

In an embodiment, a system for preparing a radiation image of a target according to the radiation imaging method 100 is provided. The system includes at least one detector module for measuring radiation emission activity of a target according to the projection measurement step ST10, and computerized components for processing data and preparing a radiation image according to the steps of energy re-binning ST20, projection separation ST30, resolution recovery ST40, image reconstruction ST50, and image consolidation and quantitative analysis ST60.

APPLICATION EXAMPLES

Applications of the imaging method 100 may be broadly categorized into three categories: 1) imaging stationary object(s) in a 3D space, 2) imaging object(s) with a linear motion, and 3) imaging rotating object(s). In all cases, the 3D imaging may be performed from measurements of two independent 2D projections. Preferably, the projections are measured orthogonal to each other, which however it is not a necessary condition.

Examples of the first application category is imaging of stationary target objects in 3D space which includes monitoring a building, imaging power plant or reactor(s), imaging radioactive waste, monitoring nuclear waste storage room, imaging hot cells, etc.

For this application category, any system configured to measure at least two 2D projections by scanning, for example, a single detector module with a raster scan motion, or an array of a detector module with a linear scan motion, may be used.

Figure 12:
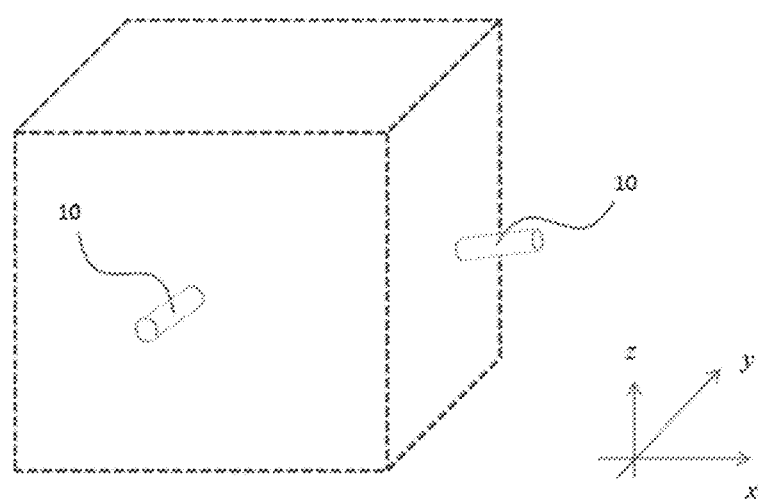
FIG. 12 is a schematic illustration of a 3D volume imaging application according to an embodiment.

In an embodiment, two single detector modules 10, each of which is arranged at a center of a 2D projection space, may be used to conduct a raster scan in a polar coordinate by tilting and rotate motion, as shown in FIG. 12. Each detector module 10 measures two 2D projections on an x-z plain and a y-z plain. In some embodiments, a Polar coordinate data collected by tilting and rotating motion of detector module 10 may be translated to a Cartesian coordinate data.

Figure 16:
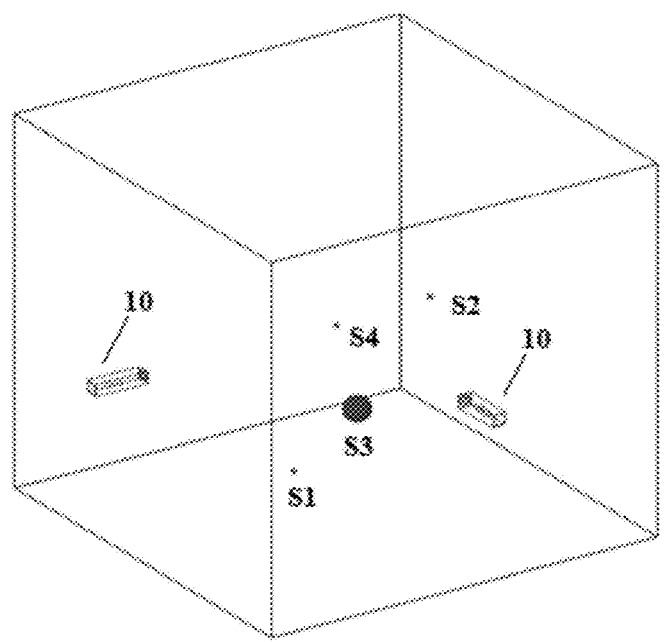
FIG. 16 is an schematic illustration of a three dimensional target space including four radiation sources and two radiation detector modules according to an embodiment.
Figure 16:
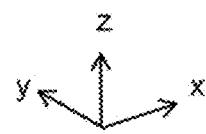

To facilitate understanding of this application category, a 3D simulation was conducted using a GATE simulation tool disclosed in Jan, S., et al. (See above Reference 14.) A target imaging space for simulation had a volume of 3×3×3 m³ and included four "hot spot"-like radioactive sources S1, S2, S3, S4, as illustrated in FIG. 16. The conditions of the simulation are summarized in Table 2. FIG. 16 illustrates the location of each if the sources S1, S2, S3, S4, and two detector modules 10.

TABLE 2

| | 3D Simulation Conditions | | | | |
|---|---|---|---|---|---|
| Radioactive Source | Location (x, y, z) cm | Shape | Radius (cm) | Activity (μCi) | Energy (keV) |
| S1 | (50, 50, 100) | sphere | 1 | 300 | 662 |
| S2 | (170, 70, 200) | sphere | 1 | 100 | 662 |
| S3 | (200, 200, 50) | sphere | 10 | 100 | 662 |
| S4 | (150, 150, 150) | sphere | 1 | 100 | 662 |

Figure 17A:
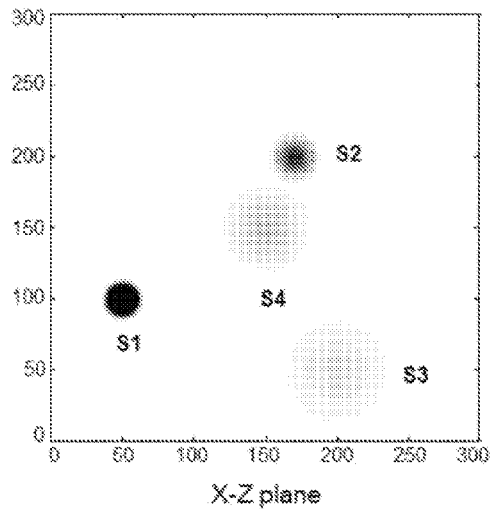
FIG. 17(A) is uncorrected 2D projection measurements of the target space of FIG. 16 in an x-y plain.
Figure 17B:
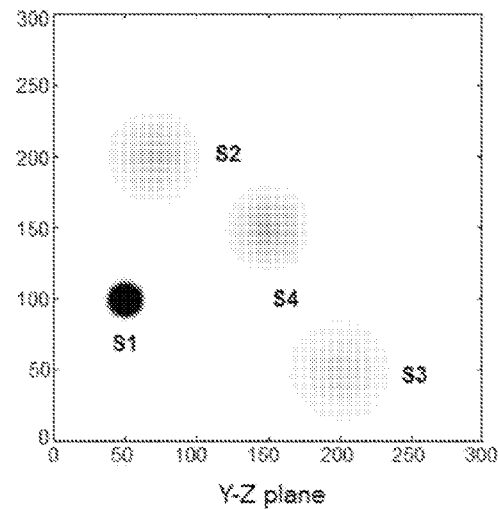
FIG. 17(B) is uncorrected 2D projection measurements of the target space of FIG. 16 in an x-z plain.

2D projection measurements were collected during the simulation. FIG. 17(A) is uncorrected 2D projections in x-y plain, and FIG. 17(B) is uncorrected 2D projections in x-z plain from the measurements taken during the simulation.

Figure 18A:
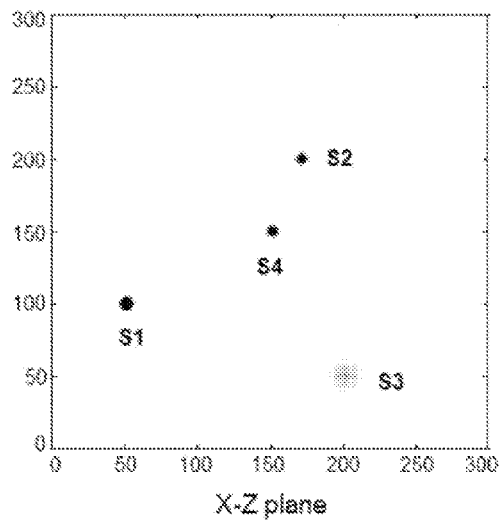
FIG. 18(A) is corrected 2D projection measurements of the target space of FIG. 16 in an x-y plain according to an embodiment.
Figure 18B:
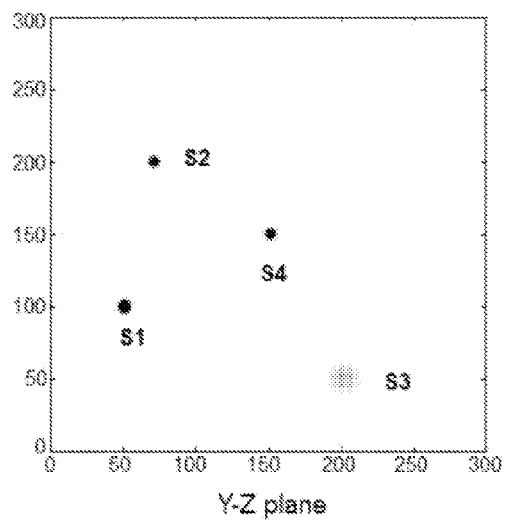
FIG. 18(B) is corrected 2D projection measurements of the target space of FIG. 16 in an x-z plain according to an embodiment.
Figure 19:
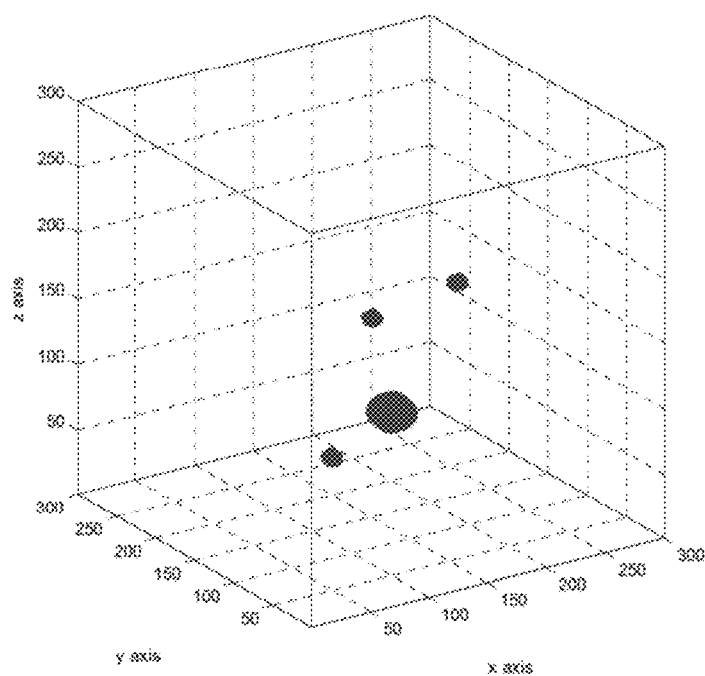
FIG. 19 is a reconstructed 3D image prepared using the corrected projection measurements of FIGS. 18(A) and 18(B) using a maximum likelihood expectation maximization (MLEM) method according to an embodiment.

FIG. 18(A) is corrected 2D projections in x-y plain after the resolution recovery step ST40 of the imaging method 100, and FIG. 18(B) is corrected 2D projections in x-z plain after the resolution recovery step ST40. FIG. 19 shows a 3D image reconstructed by combining the two resolution recovered 2D projections of FIGS. 18(A) and 18(B) using MLEM.

Figure 13:
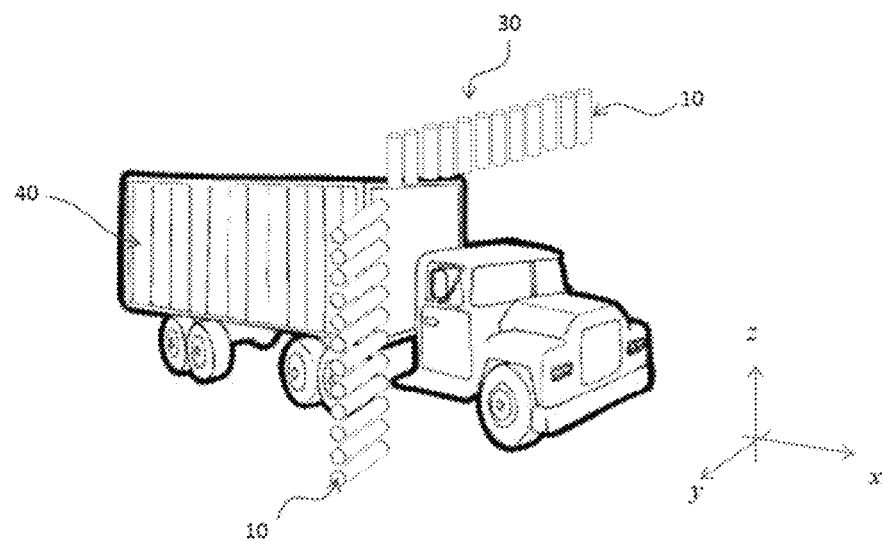
FIG. 13 is a schematic illustration of a moving object imaging application according to an embodiment.

Examples of the second application category include imaging a linearly moving vehicle at border inspection gate and imaging baggage or goods on a linearly moving conveyer. In such cases, two 2D projections are measures when an object moving in a linear motion passes through an inspection system comprising two stationary arrays of detector module 10. An example of a vehicle inspection system is illustrated in FIG. 13. As shown, stationary detector arrays 30 are arrange parallel to z-axis and y-axis, wherein a vehicle 40 moves through the detector arrays 30 in x-axis direction. Such a combination of two detector arrays 30 and a linearly moving object 40 provides two 2 D projections on x-y and x-z plains.

Figure 14:
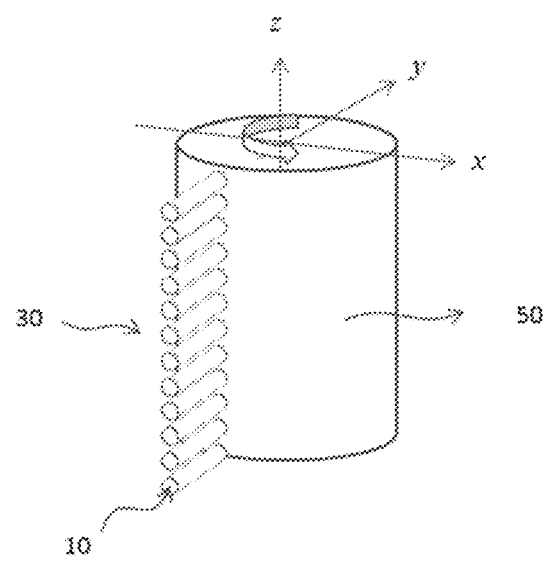
FIG. 14 is a schematic illustration of a rotating object imaging application according to an embodiment.
Figure 15:
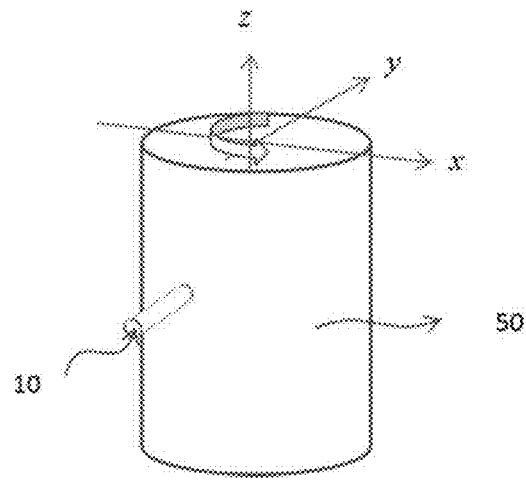
FIG. 15 is a schematic illustration of a rotating object imaging application according to another embodiment.

An example of the third application category is imaging of a waste drum. Similar to the second application category, a target object provides a motion in this example. As such, only one detector module with 2D a scanning motion or an array of detectors with a 1D linear motion may be used to scan for a 3D imaging reconstruction. Exemplary drum inspection systems are illustrated in FIGS. 14 and 15. In FIG. 14, an array of detectors 30 scans along x-axis (x-z plain), and an object 50 is rotated by 90°, and scanning of the object along the x-axis is repeated (y-z plain). This generates two 2D projections for a 3D reconstruction. Similarly, as shown in FIG. 15, a single detector module 10 may conduct a raster scan to cover x-z plain, and another scan may be taken after the object 50 is rotated 90° for y-z plain 2D projections.

According to embodiments, a detector module 10 or an array of detector modules 30 may be used for the imaging method 100 for various applications to provide substantial sensitivity improvements over prior art systems. In some embodiments, the imaging methods according to embodiments of the present disclosure may be used with any type of gamma imaging systems configured to provide 2D projections.

All patents referred to herein, are hereby incorporated herein in their entirety, by reference, whether or not specifically indicated as such within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present disclosure. It is to be understood that no limitation with respect to the specific embodiments illustrated is intended or should be inferred. The disclosure is intended to cover by the appended claims all such modifications as fall within the scope of the claims.

What is claimed is:

1. A radiation imaging method, comprising the steps of:
    collecting radiation emission data from a target including at least one radiation source, wherein the data includes measurements from at least two projections;
    classifying the data into at least one energy range;
    separating the data in each energy range into N independent radiation distributions, wherein N is a number of the radiation sources, and each of the N independent radiation distributions corresponds to each of the radiation sources;
    processing the data in each of the N independent radiation distributions to estimate its true distribution; and
    reconstructing a radiation distribution image of the target using the processed data
    wherein the step of separating the data into N independent radiation distributions comprises approximating the data in each of the energy ranges as a Gaussian mixture of N independent Gaussian distributions according to the equation:

$$P(x) = \sum_{n=1}^{N} \pi_n N(x \mid \mu_n, \Sigma_n)$$

wherein $x=(x^1, x^2, \ldots, x^d)$ for d dimension and mixing coefficient $\pi_n$ is denoted weight of each component Gaussian distribution, which satisfies an equation:

$$\sum_{n=1}^{N} \pi_n = 1$$

wherein each component $N(x \mid \mu_n, \Sigma_n)$ is multivariate Gaussian distribution:

$$N(x \mid \mu_n, \Sigma_n) = \frac{1}{(2\pi|\Sigma_n|)^{1/2}} e^{-\frac{1}{2}(x-\mu_n)^T \Sigma_n^{-1} (x-\mu_n)}$$

wherein $\mu_n, \Sigma_n$ are marked mean and covariance of Gaussian distribution; and
finding a solution that maximize the equation:

$$\ln\{p(X)\} = \sum_{m=1}^{M} \ln p(x_m) = \sum_{m=1}^{M} \ln\left\{\sum_{n=1}^{N} \pi_n N(x_m \mid \mu_n, \Sigma_n)\right\}.$$

2. The radiation imaging method of claim 1, wherein the at least two projections are measured using a radiation detector module.

3. The radiation imaging method of claim 2, wherein the detector module comprises a collimator, a scintillator, and a photo sensor.

4. The radiation imaging method of claim 3, wherein the collimator is a flat field collimator having an opening diameter about 25 mm to about 76 mm, and the scintillator has a thickness of about 25 mm to about 127 mm.

5. The radiation imaging method of claim 2, wherein the radiation detector module is an imaging detector having an n×m intrinsic spatial resolution.

6. The radiation imaging method of claim 2, wherein the radiation detector measures projections from at least one angle view in a 2D or 3D space by conducting at least one selected motion from raster scan, linear, tilt or rotating motion.

7. The radiation imaging method of claim 1, wherein the at least two projections are measured using an array of radiation detector modules.

8. The radiation imaging method of claim 1, wherein the parameters $\pi_n, \mu_n, \Sigma_n$ are calculated using an ML (maximum likelihood) method or an expectation maximization (EM) method.

9. The radiation imaging method of claim 1, wherein the step of processing the data to estimate the true distribution is performed using a point spread function, wherein the point spread function is a function of a distance between a detector and a radiation source, energy of the radiation source, and attenuation, which depends on a material composition of a target imaging space, wherein the point spread function is empirically measured or estimated by a simulation method.

10. The radiation imaging method of claim 1, wherein the step of processing the data to estimate the true distribution is performed using a transfer function.

11. The radiation imaging method of claim 1, wherein the step of reconstructing a radiation distribution image uses a maximum likelihood expectation maximization (MLEM) based reconstruction algorithm or a statistics based reconstruction algorithm.

12. The radiation imaging method of claim 1, wherein the step of classifying the data includes classifying the data into a plurality of energy ranges, wherein the method further includes the step of consolidating the radiation distribution images from the plurality of energy ranges.

13. The radiation imaging method of claim 12, wherein the step of reconstruction a radiation distribution image further provides quantitative and spectroscopic information.

14. The radiation imaging method of claim 12, wherein consolidating the radiation distribution images includes superimposing the reconstructed radiation images and video images of the target space to identify locations of radiation sources, wherein images created from superimposing radiation images and video images are displayed using a virtual reality technique.

15. A radiation imaging method, comprising the steps of:
collecting radiation emission data from a target including at least one radiation source, wherein the data includes measurements from at least two projections;
classifying the data into at least one energy range;
separating the data in each energy range into N independent radiation distributions, wherein N is a number of the radiation sources, and each of the N independent radiation distributions corresponds to each of the radiation sources;
processing the data in each of the N independent radiation distributions to estimate its true distribution; and
reconstructing a radiation distribution image of the target using the processed data;
wherein the step of processing the data in each of the N independent radiation distributions to estimate its true distribution comprises calculating a deconvolution between each of the projections and a point spread function by solving an equation:

$$T(x) = \sum_{n=1}^{N} \{decon(P_n(x), psf_n(x))\}$$

wherein, $T(x) = \Sigma T_n(x)$, $T_n(x)$ is a true response function of $n^{th}$ distribution and $psf_n(x)$ is a point spread function corresponding to a distance of a radiation source of $T_n(x)$, and $P_n(x)$ is a separated $n^{th}$ Gaussian profile of a projection.

16. The radiation imaging method of claim 15, wherein the step of separating the data into N independent radiation distributions includes treating the data as a probability distribution model and applying a corresponding method for separating the data into N independent distribution.

17. The radiation imaging method of claim 15, wherein the step of processing the data further recovers a shape and intensity of each of the radiation sources.

18. A system for preparing a radiation image of a target, comprising:
at least one radiation detector module for collecting radiation emission data from a target, wherein the data includes measurements from at least two projections; and
at least one computerized component configured for classifying the data into at least one energy range,
separating the data in each energy range into N independent radiation distributions, wherein N is a number of radiation sources, and each of the N independent radiation distributions corresponds to each of the radiation sources, wherein the step of separating the data into N independent radiation distributions comprises approximating the data in each of the energy ranges as a Gaussian mixture of N independent Gaussian distributions according to the equation:

$$P(x) = \sum_{n=1}^{N} \pi_n N\left(x \mid \mu_n, \sum_n\right)$$

wherein $x=(x^1, x^2, \ldots, x^d)$ for d dimension and mixing coefficient $\pi_n$ is denoted weight of each component Gaussian distribution, which satisfies an equation:

$$\sum_{n=1}^{N} \pi_n = 1$$

wherein each component $N(x|\mu_n, \Sigma_n)$ is multivariate Gaussian distribution:

$$N\left(x \mid \mu_n, \sum_n\right) = \frac{1}{(2\pi|\sum_n|)^{\frac{1}{2}}} e^{-\frac{1}{2}(x-\mu_n)^T \Sigma_n^{-1}(x-\mu_n)}$$

wherein $\mu_n, \Sigma_n$ are marked mean and covariance of Gaussian distribution; and
finding a solution that maximize the equation:

$$\ln\{p(X)\} = \sum_{m=1}^{M} \ln p(x_m) = \sum_{m=1}^{M} \ln\left\{\sum_{n=1}^{N} \pi_n N\left(x_m \mid \mu_n, \sum_n\right)\right\},$$

processing the data in each of the N independent radiation distributions to estimate its true distribution, and reconstructing a radiation distribution image of a target using the processed data.

19. The system of claim 18, wherein the system includes at least one radiation detector module, wherein the target is a two or three dimensional space including at least one stationary radiation source, wherein at least one radiation detector module are configure to measure radiation emission from the at least one stationary radiation source, wherein the at least one radiation detector module measures the projections by raster scanning, linear motion, tilting or rotating.

20. The system of claim 18, wherein the target is a moving object, wherein the system includes two arrays of stationary radiation detector modules including a first array arranged parallel to a z-axis and a second array arranged parallel to a y-axis, wherein the two arrays of stationary radiation detector modules measure radiation emission data of the target as the target moves through the two arrays of stationary radiation detector modules in an x-axis direction.

21. The system of claim 18, wherein the at least one radiation detector module scans the target in a first path along an x-axis to obtain measurements for an x-z plane, wherein the target is rotated by 90°, and the at least one radiation detector module scans a second path along the x-axis to obtain measurement for a y-z plane.

22. The system of claim 18, the detector module comprises a collimator and a radiation detector including a scintillator and at least one photo sensor.

23. The system of claim 22, wherein the collimator is a flat field collimator having an opening diameter about 25 mm to about 76 mm, and the scintillator has a thickness of about 25 mm to about 127 mm.

24. The system of claim 18, wherein the radiation detector module is an imaging detector having a collimator and an n×m intrinsic spatial resolution.

25. The system of claim 18, wherein the computerized component is configured to superimpose the radiation distribution image and video images of the target to provide locations of radiation sources, wherein superimposed images of the radiation distribution image and video images are displayed using a virtual reality technique to enhance relative radiation location in 3D space.

26. A system for preparing a radiation image of a target, comprising: at least one radiation detector module for collecting radiation emission data from a target, wherein the data includes measurements from at least two projections; and at least one computerized component configured for classifying the data into at least one energy range, separating the data in each energy range into N independent radiation separating the data in each energy range into N independent radiation distributions, wherein N is a number of radiation sources, and each of the N independent radiation distributions corresponds to each of the radiation sources, processing the data in each of the N independent radiation distributions to estimate its true distribution, wherein the step of processing the data in each of the N independent radiation distributions to estimate its true distribution comprises calculating a deconvolution between each of the projections and a point spread function by solving an equation:

$$T(x) = \sum_{n=1}^{N} \{decon(P_n(x), psf_n(x))\}$$

wherein, $T(x)=\Sigma T_n(x)$, $T_n(x)$ is a true response function of $n^{th}$ distribution and $psf_n(x)$ is a point spread function corresponding to a distance of a radiation source of $T_n(x)$ and $P_n(x)$ is a separated $n^{th}$ Gaussian profile of a projection, and reconstructing a radiation distribution image of a target using the processed data.

* * * * *

UNITED STATES PATENT AND TRADEMARK OFFICE
CERTIFICATE OF CORRECTION

PATENT NO. : 9,953,463 B2
APPLICATION NO. : 14/861384
DATED : April 24, 2018
INVENTOR(S) : Jinhun Joung It is certified that error appears in the above-identified patent and that said Letters Patent is hereby corrected as shown below:

On the Title Page

On the page 2, in Column 1, item (56), Other Publications, Line 7, delete "Cartogam" and insert -- Cartogram --, therefor.
On the page 2, in Column 1, item (56), Other Publications, Line 14, delete "Dimentional" and insert -- Dimensional --, therefor.
On the page 2, in Column 1, item (56), Other Publications, Line 18, delete "Aperature" and insert -- Aperture --, therefor.
On the page 2, in Column 2, item (56), Other Publications, Line 1, delete "Aperature" and insert -- Aperture --, therefor.

In the Specification

Column 1, Line 38, delete "et." and insert -- et --, therefor.
Column 3, Line 27, after "327" insert -- . --.
Column 3, Line 30, after "370" insert -- . --.
Column 3, Line 37, delete "Scinecne." and insert -- Science. --, therefor.
Column 3, Line 42, after "1551" insert -- . --.
Column 3, Line 47, after "581" insert -- . --.
Column 3, Line 59, delete "Communications," and insert -- Communications. --, therefor.
Column 4, Line 3, delete "et." and insert -- et --, therefor.

In the Claims

Column 16, Claim 1, Line 10, delete "data" and insert -- data; --, therefor.
Column 20, Claim 26, Lines 13-14, after "radiation" delete "separating the data in each energy range into N independent radiation".

Signed and Sealed this
Twenty-sixth Day of June, 2018

Andrei Iancu
*Director of the United States Patent and Trademark Office*